(12) United States Patent
Carson

(10) Patent No.: US 6,692,518 B2
(45) Date of Patent: Feb. 17, 2004

(54) PATIENT TEMPERATURE CONTROL SYSTEM

(75) Inventor: Gary Carson, Golden, CO (US)

(73) Assignee: Medivance Incorporated, Louisville, CO (US)

(*) Notice: Subject to any disclaimer, the term of this patent is extended or adjusted under 35 U.S.C. 154(b) by 0 days.

(21) Appl. No.: 10/087,630

(22) Filed: Feb. 27, 2002

(65) Prior Publication Data

US 2003/0163183 A1 Aug. 28, 2003

(51) Int. Cl.[7] .................. A61F 7/00; H05B 3/02
(52) U.S. Cl. .................. 607/104; 607/108; 219/428; 219/477; 219/488
(58) Field of Search .................. 607/96, 104, 108–112; 62/175, 259.3; 236/51; 165/206; 219/400, 428, 477, 480, 483, 486, 487

(56) References Cited

U.S. PATENT DOCUMENTS

| | | | |
|---|---|---|---|
| 3,007,473 A | 11/1961 | Jackson et al. | 128/400 |
| 3,064,649 A | 11/1962 | Fuson | 128/214 |
| 3,460,538 A | 8/1969 | Armstrong | 128/303.1 |
| 3,504,674 A | 4/1970 | Swenson et al. | 128/303.1 |
| 3,888,259 A | 6/1975 | Miley | 128/400 |
| 3,995,621 A | 12/1976 | Fletcher et al. | 128/2 |
| T994,001 I4 | 5/1980 | Buckberg et al. | 128/214 |
| 4,259,961 A | 4/1981 | Hood, III | 128/400 |
| 4,416,280 A | 11/1983 | Carpenter et al. | 128/399 |
| 4,427,009 A | 1/1984 | Wells et al. | 128/400 |
| 4,508,123 A | 4/1985 | Wyatt et al. | 128/692 |
| 4,512,163 A | 4/1985 | Wells et al. | 62/394 |
| 4,523,594 A | 6/1985 | Kuznetz | 128/402 |
| 4,691,762 A * | 9/1987 | Elkins et al. | 165/46 |
| 4,788,417 A * | 11/1988 | Graflind | 219/528 |
| 4,844,072 A | 7/1989 | French et al. | 128/400 |
| 4,873,995 A * | 10/1989 | Kikuchi et al. | 607/102 |
| 4,966,145 A | 10/1990 | Kikumoto et al. | 128/377 |
| 5,023,430 A * | 6/1991 | Brekkestran et al. | 219/486 |
| 5,097,829 A | 3/1992 | Quisenberry | 128/400 |
| 5,266,778 A | 11/1993 | Bailey | 219/497 |
| 5,270,005 A | 12/1993 | Raible | 422/46 |
| 5,466,216 A | 11/1995 | Brown et al. | 604/33 |
| 5,551,248 A * | 9/1996 | Derosier | 62/155 |
| 5,573,502 A | 11/1996 | LeCocq et al. | 604/4 |
| 5,609,571 A | 3/1997 | Buckberg et al. | 604/4 |
| 5,609,620 A | 3/1997 | Daily | 607/105 |
| 5,634,940 A | 6/1997 | Panyard | 607/104 |
| 5,643,191 A | 7/1997 | Buckberg et al. | 604/4 |
| 5,645,531 A | 7/1997 | Thompson et al. | 604/67 |
| 5,702,358 A | 12/1997 | Witherspoon et al. | 604/4 |
| 5,730,720 A | 3/1998 | Sites et al. | 604/27 |
| 5,817,045 A | 10/1998 | Sever, Jr. | 604/4 |
| 5,837,003 A * | 11/1998 | Ginsburg | 607/106 |
| 5,871,526 A * | 2/1999 | Gibbs et al. | 607/104 |
| 5,957,137 A | 9/1999 | Dalke et al. | 128/898 |
| 5,957,879 A | 9/1999 | Roberts et al. | 604/4 |
| RE36,386 E | 11/1999 | Abbott et al. | 604/4 |
| 5,997,816 A | 12/1999 | McIntosh et al. | 422/44 |
| 6,019,783 A | 2/2000 | Philips et al. | 607/105 |
| 6,042,559 A | 3/2000 | Dobak, III | 604/7 |

(List continued on next page.)

Primary Examiner—Roy D. Gibson
(74) Attorney, Agent, or Firm—Marsh Fischmann & Breyfogle LLP

(57) ABSTRACT

A temperature control system provides for the optimal management of patient temperature during a surgical procedure, such as those which require the patient to on bypass. The system employs a plurality of controllers as well as a plurality of temperature control means in order to provide optimal temperature control. In one configuration of the invention, controllers for each of the heat exchange devices may be interconnected using a data link. The connection may provide for a master/slave relationship wherein temperature sensors included in each system are employable as temperature feedback for initiating temperature changes. This device may be configured such that it operates in conjunction with another device or provides stand alone temperature control.

29 Claims, 7 Drawing Sheets

U.S. PATENT DOCUMENTS

| | | | |
|---|---|---|---|
| 6,086,609 A | * 7/2000 | Buckley | 607/104 |
| 6,095,992 A | 8/2000 | Augustine | 602/2 |
| 6,110,139 A | 8/2000 | Loubser | 604/30 |
| 6,126,080 A | * 10/2000 | Wada | 236/51 |
| 6,146,411 A | 11/2000 | Noda et al. | 604/105 |
| 6,149,674 A | 11/2000 | Borders | 607/96 |
| 6,197,045 B1 | 3/2001 | Carson | 607/104 |
| 6,254,626 B1 | 7/2001 | Dobak, III et al. | 607/105 |
| 6,261,312 B1 | 7/2001 | Dobak, III et al. | 607/105 |
| 6,376,805 B2 | * 4/2002 | Faries et al. | 219/219 |
| 6,517,510 B1 | * 2/2003 | Stewart et al. | 604/31 |
| 6,624,394 B2 | * 9/2003 | Chasen et al. | 219/486 |

* cited by examiner

PATIENT TEMPERATURE CONTROL SYSTEM

FIELD OF THE INVENTION

The present invention relates to a system for optimally controlling patient temperature during a surgical procedure, and more specifically to a temperature control system which employs a plurality of heat exchange devices controlled by a central controller.

BACKGROUND OF THE INVENTION

Cardiovascular surgery though safe and effective has inherent risk associated with the artificial oxygenation and pumping of the patient's blood over extended periods of time. Some primary sources of morbidity is micro air, particulates and activated blood components that may lodge in the vasculature causing diffuse ischemic sites. One way to minimize organ damage during such a procedure is through the inducement of hypothermia. Hypothermia has been shown to bestow protection to the heart, brain, kidneys, liver and spine.

Hypothermia during a cardiovascular procedure may be induced by cooling blood in the bypass circuit. Temperature control has been provided through use of a device such as a blood oxygenator, which includes a blood/water heat exchanger. In such a system, blood temperature is controlled by controlling water temperature on the opposite side of the water/blood heat exchanger in the circuit. The perfusionist running the equipment determines the correct water setting and duration of temperature changes in order to achieve a desired patient core temperature.

Upon completion of a cardiovascular procedure, hypothermia must be reversed as quickly as possible. This typically must be done prior to the patient awaking from anesthesia to prevent detrimental affects of hypothermia. Mild hypothermia in the medical or the surgical patient has been thought to prolong the time to extubation, contribute to coagulopathies, increase the chance of infection, and increase cardiac demand as a result of shivering.

As part of the surgical procedure, a typical method for rapid re-warming at the end of the case is to heat the blood in the heart/lung circuit. In order to achieve a normothermic core temperature, while minimizing the time on bypass, the blood temperature is often raised to hyperthermic levels. Research has indicated that maintaining a small differential between arterial blood temperature and brain temperature provides for an optimal therapy. This would typically require feedback control from a sensor close to the brain, or controlling the rate of blood temperature rise to minimize the difference. Further, even when the core temperature is raised to normothermic temperatures with the bypass circuit, without extending the time at temperature, an afterdrop occurs postoperatively due to re-distribution of cold peripheral blood into the core.

SUMMARY OF THE INVENTION

The inventors have recognized that to provide optimal patient temperature control during a surgical procedure a plurality of temperature control systems, each in communication with a central controller, may be employed. Further, the inventors have recognized that a system which provides temperature control of the blood in a bypass circuit in addition to temperature control of the periphery of the patient's body may achieve the benefits of optimal temperature control during the inducement of hypothermia as well as minimizing any potential detrimental affects during patient re-warm.

Described herein is a patient's temperature control system which employs a plurality of heat exchange devices. Each heat exchange device is configured to affect temperature in one or more patient regions. For example, heat exchange devices may comprise a set of temperature control pads which provide heating and cooling to the periphery of a patient, as well as a blood/water heat exchanger which provides temperature control for patient blood while on bypass. Further, the system includes at least one controller configured to receive measured temperature signals from a plurality of temperature sensors, said controller further configured to generate and transmit control signals to each of the plurality of heat exchange devices so as to affect one or more measured patient temperatures. The plurality of heat exchange devices is each further configured to receive the control signals and perform the heat exchange to the designated region according to the received control signal.

In one configuration of the invention, the measured patient temperatures may comprise the core body temperature, patient blood temperature, as well as a temperature for the heat exchange medium (e.g., water) employed in the heat exchange device. The core body temperature may be measured in such locations as the nasopharynegeal region, the bladder, and/or the rectal region.

The controller described herein may be further configured to include, store and employ target temperatures to be met and maintained by the heat exchange devices during one or more modes of operation. These modes of operation may correspond to portions of a surgical procedure. For example, during a cardiovascular procedure different target temperatures may be established prior to intubation, after intubation, while on bypass, prior to extubation, and finally post-operatively.

In one configuration of the invention, each of the plurality of patient heat exchange devices may be part of a stand-alone temperature control system, each of which includes a controller configured to control a particular heat exchange device independent of any other temperature control systems. According to the invention described herein, each of the temperature control systems patient heat exchange devices may be further configured to be connectable to at least one other temperature control system so that both systems may operate under centralized control. In yet another configuration of the invention, the relationship between the controllers of each system may be that of a master/slave. The connection between the systems may be established through use of a communication protocol such as RS-232 through a port in a housing for each of the temperature control systems. The connection may be a direct electrical connection using a cable or other devices such as wireless communication connections may be employed.

As mentioned above, the controller may be configured as part of a temperature control system which is connectable to one or more heat exchange devices. In one configuration of the invention, the temperature control system may comprise one or more reservoirs for storing and circulating water through the one or more heat exchange devices, such as control pads which are positionable on a the periphery of a patient and/or a blood/water heat exchanger and oxygenator. The controller may be further configured to employ one or more predictive algorithms for controlling water temperature.

The system described herein may further include at least one interactive display through which patient temperature information may be presented and various modes of operation initiated. Specifically, the interactive display may include one or more display screens which present information such as temperatures being monitored at different locations. These temperatures may include core body temperature, patient blood temperature, as well as water temperatures within the temperature control systems. Further, the display may include various input devices so that a system user may scroll through various items of operational information such as modes of operation stored in memory, and select a desired mode. Prior to operation, various programming such as instructions for simultaneous control of multiple heat exchange devices as well as target temperature during various modes of operation may be entered through the interactive display.

In the configuration of the invention, where one or more temperature control systems are connected in a master/slave relationship, a controller of a designated temperature control system may be identified as a master (central) controller. The central controller may be provided with programming for controlling one or more slave temperature control systems. Further, the display in the master temperature control system (s) may be configured to present temperature and other operational information received by the temperature control system connected as slave(s). Once the data link for master and slave controllers are disconnected, the stand-alone temperature control systems may then operate independently.

Prior to beginning a surgical procedure, heat exchange devices to be used are positioned so as to provide heat exchange to a patient in a desired region. For example, temperature control pads are positioned on the periphery of the patient and connected to the temperature control system. Further, a core body temperature sensor is connectable to one of the temperature control systems, which in one configuration of the invention may be the temperature control system for the temperature control pads. Blood temperature may be controlled through a blood/water heat exchanger and oxygenator which circulates the blood of the patient while on bypass. During a surgical procedure, a master controller may receive temperature signals from a plurality of temperatures sensors configured for measuring selected patient and system temperatures. Prior to the initiation of the surgical procedure, certain target temperatures are identified as well as modes of operation are identified which are stored in memory. This information may be entered through the interactive user interface.

During a surgical procedure, one or more modes of operation may be employed for providing optimal patient temperature control. Through use of the interactive display incorporated in the master temperature control system, a particular mode of operation may be identified and selected. Once the surgical procedure has begun, the mode of operation may be initiated by a system operator (e.g. perfusionist). For example, during a surgical procedure which requires a patient to go on bypass, different modes of operation may be established prior to intubation, before cannulation, while the patient is on bypass, re-warm prior to extubation, and postoperatively.

For example, in the configuration of the system described herein where the heating devices comprise a blood/water heat exchanger and temperature control pads, during the initial phase after intubation (prior to going on bypass) the temperature control pads are employable for lowering the core body temperature of the patient to a desired level. Once this core body temperature is achieved cannulation and initiation of heart-lung bypass may be performed. While on bypass, a core body temperature may be maintained through monitoring and use of the blood/water heat exchanger. Moderate rewarming of the periphery of the patient may be had through control of the temperature control pads. The core body temperature is controlled through adjustment of water temperature according to a predictive algorithm.

Upon completion of the surgical procedure, a patient re-warm may be performed through raising of the pad temperatures. During the re-warm the core body temperature can be accurately controlled using the blood/water heat exchanger. Once off bypass the control pads are used to control temperature exclusively and the data link between the temperature control systems may be terminated.

DETAILED DESCRIPTION

Figure 1:
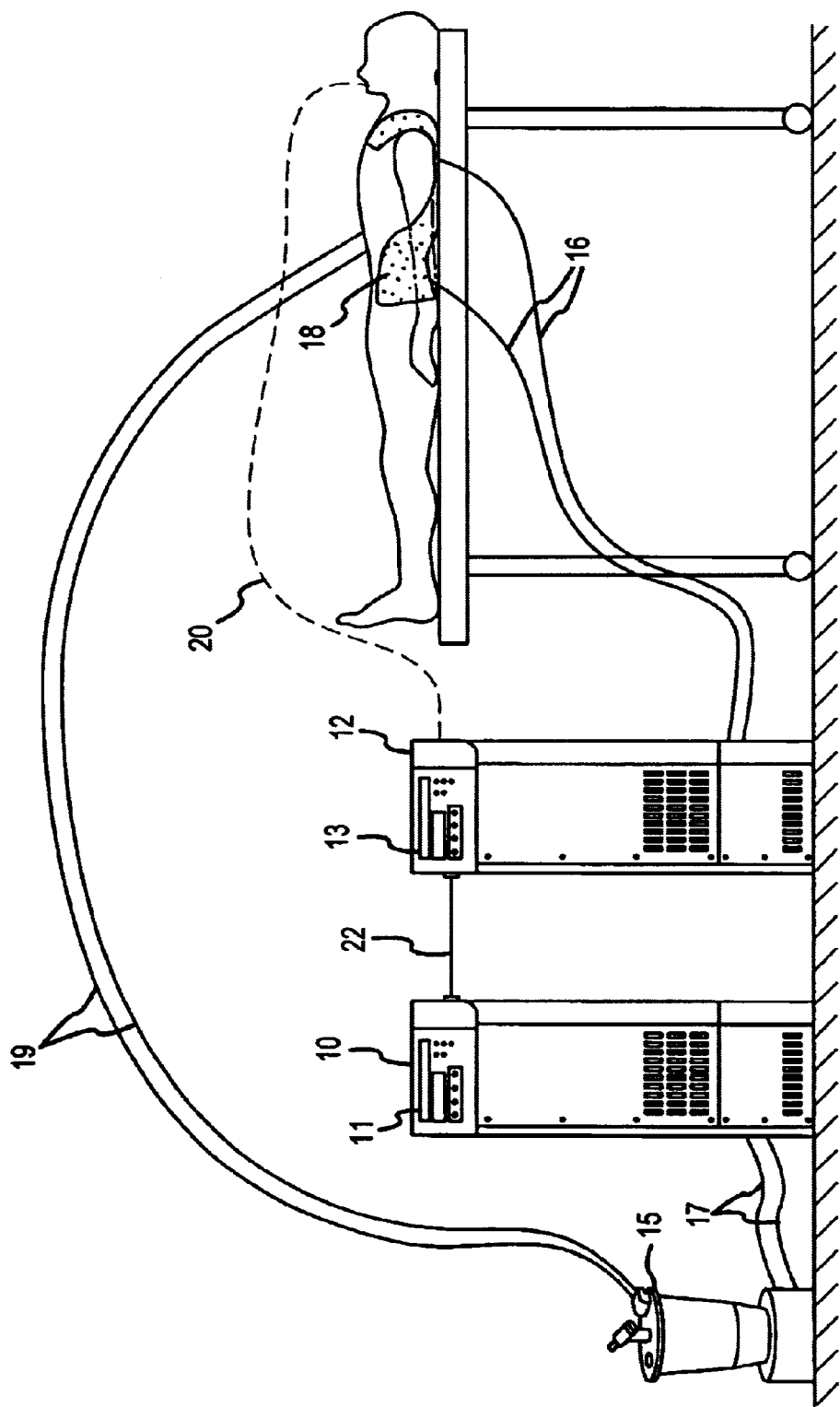
FIG. 1 is a diagrammatic view of an exemplary use of the present invention.

Disclosed in FIG. 1 is a diagrammatic representation of the system described herein. Included as part of the system is a blood/water heat exchanger temperature control system 10 which is configured to provide a heat exchange medium (e.g., water) to the blood/water heat exchanger and oxygenator 15. The blood/water heat exchanger 15 may be of the water type, wherein water is heated or cooled and then placed in proximity to the circulating blood to provide for temperature control. The blood/water heat exchanger may further include an oxygenator for providing artificial oxygenation of a patient's blood over extended periods of time. The blood/water heat exchanger 15 is connectable to the patient via supply and return lines 19. The blood/water heat exchanger may be of the type which are commercially available and typically employed for blood oxygenation for patients on bypass.

The heating and cooling of the water is performed within blood/water heat exchanger temperature control system 10. The temperature controlled water is provided to the blood/water heat exchanger via supply and return lines 17. As will be described in greater detail below, the blood/water heat exchanger includes a number of reservoirs, pumps, and heat exchange devices for providing water at optimum temperature to the blood/water heat exchanger 15.

The blood/water heat exchange temperature control system 10 further includes electronics for monitoring water temperature to be circulated within the heat exchanger 15. Water temperature and other operational information may be monitored visually through the user interface 11 incorporated in temperature control system 10. Also includable in user interface 11 are a number of selectable user inputs through which a system operator may initiate a number of preprogrammed functions for providing a desired type of temperature control.

Further shown in FIG. 1 is the contact pad temperature control system 12. The temperature control system a 12 may be selectively interconnected to one or more contact pads 18 which are configured for heating/cooling a patient during a surgical procedure. By way of example, pads 18 may be of the type described in U.S. Pat. No. 6,197,045, which is hereby incorporated, in its entirety, by reference. Temperature control system 12 includes circulating pump for drawing fluid (e.g. water) through pads under negative pressure and further include a number of reservoirs containing water used in heating or cooling. The temperature controlled water is liquid circulated through lines 16 to the pads 18 which are positionable in contact with the patient.

FIG. 1 also illustrates the interconnection of one or more external patient sensor(s) 20 interconnected with one or more of the temperature control systems, in this case the control system 12. Patient temperature sensors 20 may comprise, for example, one or more core temperature sensors (e.g. nasopharynegeal, esophageal, bladder, tympanic and rectal probes) that provide analog signals to the controller in the heat exchanger system 12. As will be disclosed in greater detail below, the temperature signals received from the patient temperature sensor 20 are employable as a feedback signal in controlling the rate of heat exchange for either the blood/water heat exchanger or the temperature control pads.

Further included in the temperature control system of FIG. 1, is a data link 22 establishable between the blood/water temperature control system 10 and the contact pad temperature control system 12. Data link 22 may comprise a cable connected between two communications ports (such as those which are employable with a protocol such as RS-232) in the temperature control systems. Other connections employable includes radio frequency wireless link, as well as any type of data link connectable between two microprocessors controlled systems. In general, the data link provides the capability for temperature control systems 10 and 12 to communicate such that patient temperature can be optimally controlled through use of a plurality of heat exchange devices.

Both the temperature control systems 10 and 12 are configured to control the temperature of water, and to provide for the circulation of the water through a heat exchange device such as the blood/water heat exchanger 15 and the temperature control pads 18. The hydraulic and electrical configuration for the temperature control systems may be substantially identical. That is to say, that either system may be easily configured to provide temperature controlled water to a number of different heat exchange devices. Further, the temperature control systems may be further configured such that they are both incorporated in a single device which is connectable to a plurality of heat exchange devices.

Figure 2:
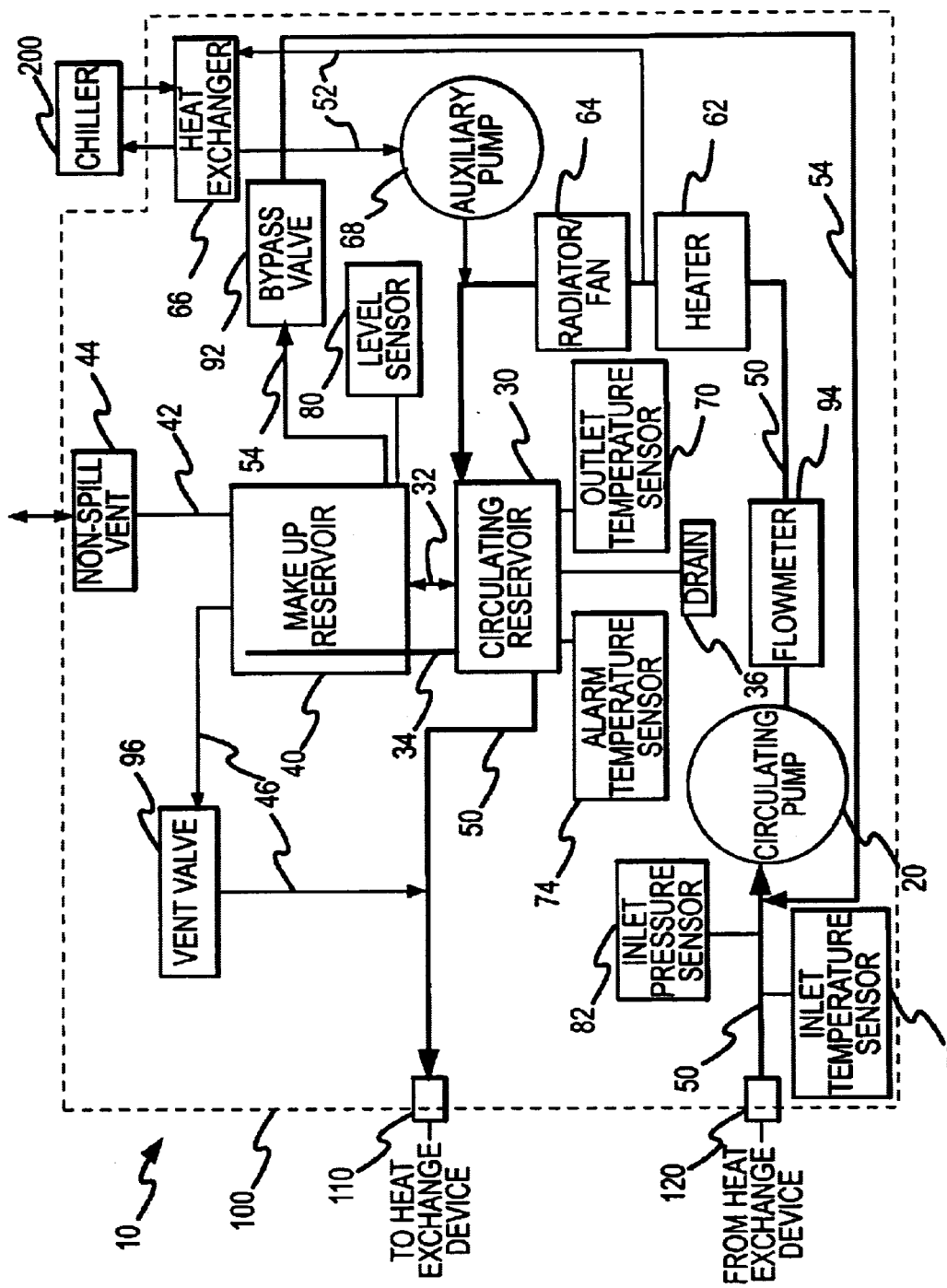
FIG. 2 discloses a hydraulic schematic of one embodiment of the temperature control system which is connectable to both the water/blood heat exchanger and oxygenator, and at least one temperature control pad.

Disclosed in a FIG. 2 is an exemplary embodiment of the hydraulic portion of the temperature control systems employable with both the blood/water heat exchanger and the control pad. One skilled in the art would realize that any number of water circulating systems may be employable in the present invention and the system disclosed in FIG. 2 is one example. Included in the system is a circulating pump 20 for drawing fluid (e.g. water) through the remote heat exchange apparatus under negative pressure, a circulating reservoir 30 and make up reservoir 40 for containing fluid, and controllable heat exchange device 62, 64 (e.g., an electric heater for fluid heating and radiator/fan for room temperature fluid cooling) for heating/cooling fluid circulated through the system.

A main fluid line 50 fluidly interconnects the system componentry. A secondary fluid line 52 may be fluidly interconnected at each end to the main fluid line 50 with an in-line heat exchange device 66 to effect further selective fluid cooling/heating via an external interface. Additionally, a fluid bypass line 54, including a bypass valve 92, may be fluidly connected between reservoir 40 and circulating pump 24 for selective fluid conditioning purposes.

Reservoirs 30 and 40, circulating pump 20, heat exchange devices 62, 64 and 66, and noted fluid lines 50, 52 and 54, all may be located within a common housing 100. Housing 100 may be provided with a selectively openable/closeable fluid output port 110 and fluid input port 124 for selective fluid interconnection with the remotely located heat exchange device.

As will be further described, during filling/emptying of the heat exchange devices fluid flows from the circulating reservoir 30 into heat exchange devices and from/to make-up reservoir 40 to/from circulating reservoir 30. During normal patient heating/cooling operations, fluid is circulated through the circulating reservoir 30, heat exchange device (s), and heat exchange devices 62 and 64 and/or 66, substantially free from passage through the make-up reservoir 40.

Circulating reservoir 30 may be physically located below the make-up reservoir 40, with a fluid interconnection line 32 extending therebetween. In the embodiment shown in FIG. 2, the top of the circulating reservoir 30 is located below the bottom of the make-up reservoir 40. As will become apparent, such an arrangement provides for the gravity flow of fluid flow from make-up reservoir 40 into circulating reservoir 30. Relatedly make-up reservoir 40 may be physically located lower than heat exchange device (s) when interconnected.

During operation, gas within circulating reservoir 30 may rise through fluid interconnection line 32 into the make-up reservoir 40. Further, a vent line 34 may be provided at the top of circulating reservoir 30 for gas removal therefrom. Vent line 34 may be vented through a non-spill outlet to the atmosphere or, as shown in FIG. 1, may be vented into the make-up reservoir 40. In turn, make-up reservoir 40 may be provided with a vent line 42 having a non-spill outlet 44 to the atmosphere. Vent 44 functions to maintain atmospheric pressure (e.g. about 14.7 psi) within the make-up reservoir 40.

As may be appreciated, the inclusion of vent lines 34 and 42 advantageously provides for the removal of gaseous bubbles from the fluid circulated through heat exchange device(s). In this regard, it should be noted that if a leak develops in the fluid circuit located outside of system 10 (e.g., a leak in the heat exchange device(s)), air will be drawn through the leak into the system 10 due to the negative pressure operating condition generated by circulating pump 20. In turn, such air will ultimately be exhausted from make-up reservoir 40 via the non-spill vent 44.

For purposes of emptying fluid from the heat exchange device(s), the system 10 may include a vent line 46 interconnected at one end to the main fluid line 50 downstream of the circulating reservoir 30. The other end of vent line 46 may be interconnected to the top of make-up reservoir 40. A controllable vent valve 90 may be interposed along the vent line 46 at a physical location above the make-up reservoir 40 to provide for selective gas flow therethrough. More particularly, to empty the heat exchange device(s), vent valve 90 may be selectively opened while circulating pump 20 is operating. In turn, air will be drawn through the vent 44, make-up reservoir 40, and vent valve 90 into the main fluid line 50 for passage through and purging of fluid within the heat exchange device(s). At the same time, the fluid within the heat exchange device(s) will be drawn therefrom by circulating pump 20 and thereafter collected in the make-up reservoir 40 via passage through the circulating reservoir 30.

Fluid may be removed from the system 10 via a drain 36 fluidly interconnected to and located below the circulating reservoir 30. When the heat exchange device(s) are disconnected from the system 10, fluid may be readily introduced into the system 10 via the outlet port 110.

The heat exchange devices 62, 64 and 66 may all be located downstream of the circulating pump 20 and upstream of the circulating reservoir 30. Such positioning isolates the pressure drop associated with these components to the positive pressure side of circulating pump 20, thereby enhancing the ability of pump 20 to maintain the desired negative pressure within the heat exchange device(s).

As further illustrated in FIG. 2, a separately controllable auxiliary pump 68 may be interposed along the secondary fluid line 52 for selectively circulating fluid through the heat exchange device 66. The heat exchanger device 66 may be disposed at a location within housing 100 that facilitates convenient interconnection with an external cooling and/or heating source. In one arrangement, the heat exchange device 66 may comprise a two-sided exchanger located in the bottom of housing 100, wherein fluid is circulated from an external chiller 200 through one side of the heat exchanger 66 and back through the chiller 200, wherein fluid within system 10 is passed through the other side of the heat exchanger 66 for enhanced cooling purposes. The speed of auxiliary pump 68 may be selectively controlled to affect the desired degree of fluid cooling/heating at exchanger 66. The provision of a secondary fluid line 52 as described above allows large and heavy refrigeration or heating equipment to be utilized in combination with system, yet be physically separated from system.

With further respect to fluid bypass line 54, FIG. 2 shows the fluid interconnection thereof between make-up reservoir 40 and main fluid line 50 at a location upstream of circulating pump 20 and downstream from the heat exchange device(s). The fluid bypass line 54 is routed through a controllable bypass valve 92, wherein fluid flow through the fluid bypass line 54 may be selectively controlled. In particular, bypass valve 92 may be opened to provide for the preconditioning of fluid in the system 10 prior to interconnection of the heat exchange device(s). For example, fluid may be circulated through the bypass fluid line 54 via operation of circulating pump 20 and heat exchange devices 62, 64 and/or 66, thereby achieving the desired fluid temperature prior to interconnection of the heat exchange device (s). In turn, effective patient temperature control can be more rapidly established.

In addition to the above-described fluid routing, containment and heat exchange componentry, the system 10 illustrated in FIG. 2 also comprises a number of sensors for system control and enhanced performance purposes. In particular, a level sensor 80 may be provided at make-up reservoir 40 for sensing the amount of fluid therewithin. In one arrangement, level sensor 80 may comprise a pressure sensor, wherein the amount of fluid within reservoir 40 may be determined in relation to the sensed head pressure. Such fluid level sensing may be employed in system 10 to provide for user alert, system control and/or system disablement upon sensing of fluid levels below and/or above predetermined amounts.

For purposes of establishing the desired temperature of fluid circulated through the heat exchange device(s), system 10 may utilize one or more temperature sensors. In particular, an outlet temperature sensor 70 may be located along the main fluid line 50 at a location downstream of the heat exchange devices 62, 64 and 66. In the embodiment illustrated in FIG. 2, the outlet temperature sensor 70 is provided at the circulating reservoir 30 for sensing the fluid temperature therewithin. Alternatively and/or additionally, an inlet temperature sensor 72 may be located along the main fluid line 50 at a location downstream of the heat exchange device(s) and upstream from the heat exchange devices 62, 64 and 66. In the embodiment illustrated in FIG. 2, the inlet temperature sensor 72 is located upstream from the circulating pump 20. The fluid temperature sensed by sensors 70 and/or 72 may be utilized in connection with the control of one or more of the heat exchange devices 62, 64 and 66 (e.g. by controlling operation of auxiliary pump 68), to obtain the desired temperature for fluid circulation. As will be further described, the inclusion of both an outlet fluid temperature sensor 70 and inlet temperature sensor 72 advantageously allows for the ongoing computation of the rate of thermal energy exchange between the heat exchange device(s) and a given patient, thereby yielding information employable for enhanced system performance. (e.g. control of the heat exchange devices 62, 64 and pump 68 to rapidly ramp to within a predetermined range of a "targeted" patient temperature).

In addition to temperature sensors 70 and 72, system 10 may further include an alarm fluid temperature sensor 74 located along the main fluid line 50 downstream from the heat exchange devices 62, 64, and 66. In the embodiment illustrated in FIG. 1, the alarm temperature sensor 74 is located at the circulating reservoir 30 for sensing the fluid temperature therewithin. The alarm temperature sensor 74 provides for temperature sensing that may be redundant to that of outlet temperature sensor 70, wherein any risk of circulating fluid outside of a predetermined temperature range may be substantially reduced. For example, system 10 may be provided so that upon the sensing of a fluid temperature outside of a predetermined high/low range, by either of the sensors 70 or 74, circulating pump 20 is automatically stopped.

System 10 may further include an inlet pressure sensor 82 located downstream of the interconnectable heat exchange device(s) and upstream of the circulating pump 20. More particularly, the inlet pressure sensor 82 may be located along the main fluid line 50 between the inlet port 120 and inlet side of circulating pump 20. The sensing of fluid pressure at the noted location facilitates the maintenance of a predetermined, desired negative pressure within the interconnectable heat exchange device(s). In this regard, the speed of the circulating pump 20 may be controlled in relation to the sensed fluid pressure at sensor 82. Such functionality is provided by the described arrangement regardless of whether one or a plurality of heat exchange device(s) are interconnected to the system 10.

System 10 may also include a flow meter 94 located along the main fluid line 50 downstream of circulating pump 20.

In the illustrated embodiment, the flow meter 94 is located between the circulating pump 20 and heat exchange devices 62, 64 and 66. The flow meter 94 provides for the sensing of fluid flow through the main fluid line 50, thereby facilitating the monitoring of expected versus actual fluid flow through the heat exchange device(s). In turn, such functionality allows system 10 to detect potential, undesired fluid flow obstructions (e.g., kinks in the tubing lines 3 interconnecting the heat exchange device(s) to the inlet port 110 or outlet port 120). Additionally, the monitoring of fluid flow rates facilitates the determination of patient thermal energy exchange and fluid heating/cooling control.

As indicated above, the various heat exchange devices 62, 64 and 66, pumps 20 and 68, and valves 90 and 92 may all be selectively controlled. As also noted, the identified sensors may provide information employable to achieve a number of system control functions.

Figure 3:
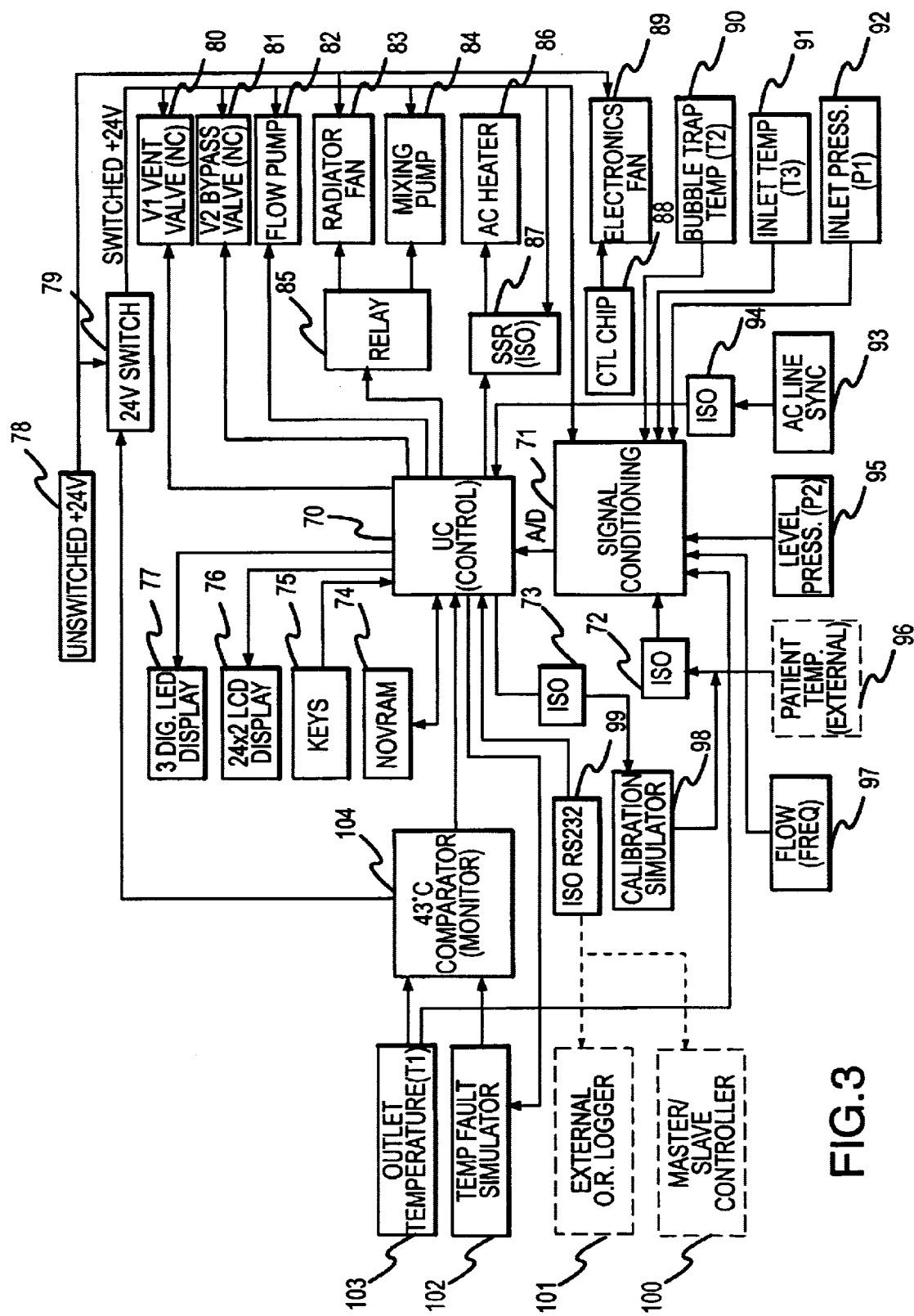
FIG. 3 discloses an electrical system diagram for the exemplary embodiment of the heating control system employable with both the blood/water heat exchanger and the temperature control pads.

To further describe the function of each of the systems and their interconnection, provided in FIG. 3 is an electrical schematic for an exemplary temperature control system which is employable with the system described in FIG. 2 to provide heating/cooling of water employable in any of the heat exchange devices described herein. As was described with respect to the hydraulic system, the electrical system is employable with any number of different heat exchange devices.

The system may include at least one controller, or microprocessor 70, interconnected to the various above noted sensors via a signal conducting interface 71. The signal condition interface 71 may comprise hardware/software for filtering, shifting, etc. of analog signals received from various sensors. Further, an A/D converter may be provided at interface 171 for processor 70 to convert the conditioned signals into digital signals for processing.

The processor 70 may be pre-programmed to process the digital signals to provide various controlled functionalities discussed herein. More particularly the processor 70 may utilize control algorithms and associated preset/user-define control limit/range stored in a memory 74 (e.g., a nonvolatile random access memory). Also includable in memory is programming for the controller to operate in a master/slave configuration when a data link is established. Target temperatures and instructions for modes of operation are also storable in memory.

For purposes of selectively modifying certain control limits sets employable with the control algorithm, as well as initiating/terminating certain system operations, system 10 may include a user interface which includes at least display devices 76 and 77, interconnected with processor 70. The user interface device may include one or more input devices (e.g., a keypad entry, touch screen, mouse with a pointer, etc.), as well as one or more displays 76 and 77. The displays 76 and 77 may display system operating conditions, setting and alarms to a user and/or prompt a user in the set-up and operation of system 10, as well as remedial actions that may be undertaken in the event of defective system condition of concern.

System 10 may be further interconnectable with a power source 78 (e.g., 24 volt dc source) that powers an internal drive circuit (not shown). In turn, the drive circuit may supply drive signals to various sensors as well as a temperature simulator 180, calibration simulator 98 and control chip 82. Additionally, power source 78 may provide drive signals via switch 79 to the vent valve 80, bypass valve 81, flow pump 82, auxiliary pump 84 and to heater 86 via solid state relay (SSR) 87. Finally, power source 78 may provide drive signals directly to radiator fan 83 and electronics fan 89.

While power source 78 supplies drive signals to each of the above fluids handling heat exchange devices, processors 70 controls the operation thereof. More particularly processor 70 may control the open/close state of vent of valve 80 and bypass valve 81. Processor 70 may also control the operation of flow pump 82 and auxiliary pump 84. Further, processor 70 can control the operation of heater 86 and radiator/fan 83 to affect the desired amount of heating and cooling. In the embodiment shown in FIG. 3, a relay 85 is interposed between the processor 70 and auxiliary pump 84 and radiator/fan 83, wherein control signal from processor 70 will be directed to radiator/fan 83 when an external heat exchanged device is not utilized, and wherein control signals from processor 70 are directed to auxiliary pump 84, when one or more external heat exchange devices are interconnected.

FIG. 3 further illustrates the interconnection of one or more external patient temperature sensors 96 with the signal conditioning interface 71. Patient temperature sensor 96 may comprise, for example, one or more bodily core temperature sensors (e.g. nasopharyngeal, esophageal, bladder, tympanic and rectal probes) that provide analog signals to the signal conditioning interface 71. In turn, the interface 71 provides digital signals to processors 70 for use in application of preset temperature control algorithms. By way of example, the temperature data received from external sensors 96 could be utilized at processor 70 to determine the amount and rate of thermal exchange to be affected by the system in relation to preset/user-defined patient (target) temperatures. In turn, processor 70 may provide the appropriate control signals to heater 86, with radiator/fan 83, and/or auxiliary pump 84.

In addition to the components described above, FIG. 3 also illustrates that connections may be established with an external operating room data logger 101 and/or another component 100 in a master/slave configuration through RS-232 Port 99. The actual connection to other components may be established using an interconnection cable employing a protocol such as RS-232 between units, or some type of wireless communications system. In one configuration of the inventions, one temperature control system may operate in a master/slave relationship with another substantially identical temperature control system when providing temperature control through operation of a plurality of heat exchange devices. As described above, the heat exchange devices may include temperature control pads and a blood/water heat exchanger.

Although both the blood/heat exchange system and the temperature control pad system are described as separate units, it is conceivable that these devices may be incorporated into a single hardware unit substantially comprising the hydraulic and electrical systems described above. A combined unit may include connections for both the temperature control pads and a blood/water heat exchanger, wherein such a device may include one or more reservoirs for holding water used in the heat exchange. Both heat exchange systems may be then controlled by a single microprocessor configured to receive input from one or more temperature sensors and control temperatures of one or more heat exchange devices.

As was described above, when the heat exchanger systems are configured in different devices, a communications link is establishable between the two devices so they may communicate using known communications protocol. Each unit may be preprogrammed to use a protocol specific to a surgical team. When the temperature control systems are connected in a mater/slave relationship, a user interface in the master temperature controller may be configured to present information for all connected temperature control systems and allow a perfusionsis to view such items which include: patient temperature, current mode of operation, and water temperature from either unit.

Figure 4:
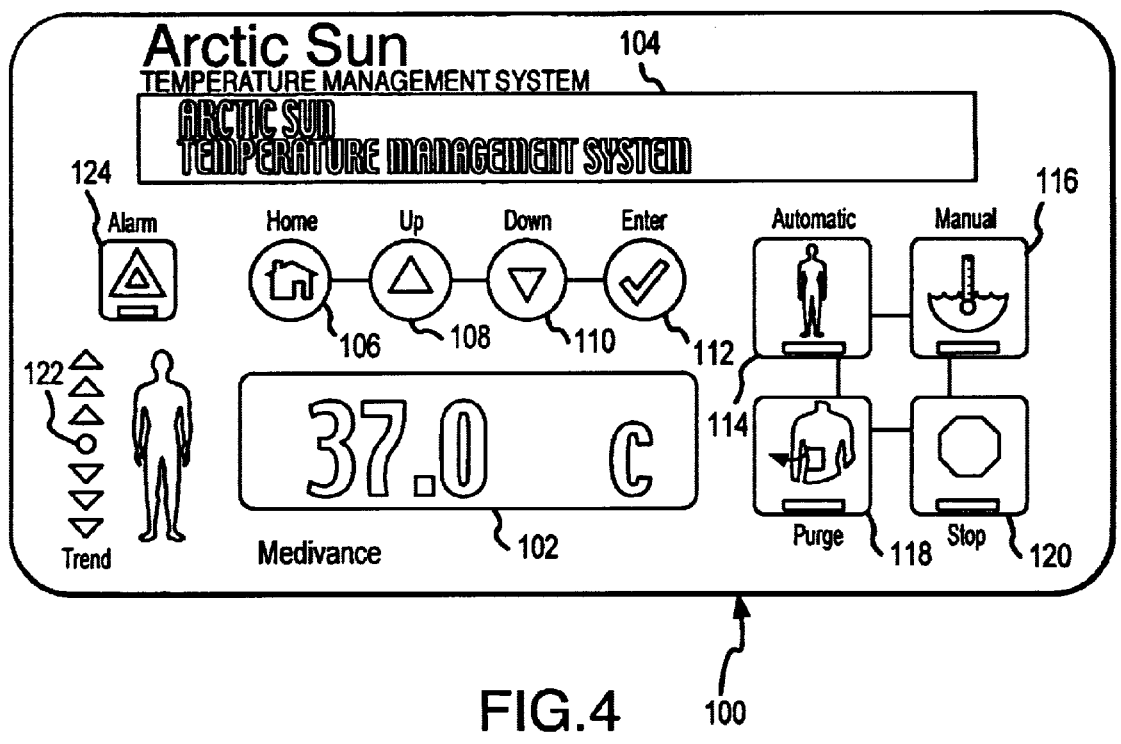
FIG. 4 discloses a front view of one embodiment of a user interface employable with the present invention.

Disclosed in FIG. 4 is one configuration of a user interface 100 which may be incorporated in any of the temperature control systems described herein. Such interface 100 will be described in relation to an exemplary application of various features of the system described above. The user interface 100 comprises user operating keys 106–120, a message screen 112, and a patient temperature display at 102. The message screen 108 displays parameter settings, warnings, mode of operation, and alarms during operation.

If one or more patient temperature sensors are utilized in a given procedure, display 102 presents the measured patient temperature. With a patient temperature sensor in place, icon 122 may comprise a plurality of upward oriented and downward oriented arrows with a circle disposed therebetween. An illuminated upward arrow indicates that a patient's temperature is rising. An illuminated downward arrow indicates that a patient's temperature is falling. The higher or a lower the illuminated arrow, the faster the temperature is changing. When only the circle is lit, the temperature of the patient is substantially constant.

Four main modes of automated operation of the system can be set utilizing keys 114–120:

1. "Patient temperature control mode" may be set by pushing key 114;
2. "Water temperature control mode" set by pushing key 116;
3. "Purge mode" set by pushing key 118;
4. "Stop mode" set by pushing key 120.

Additional information about a particular mode and modification of corresponding parameter settings may be achieved by pressing the "up arrow" key 108 or "down arrow" key 110 while in a given mode, as will be further described.

The patient temperature control mode automatically functions to monitor and control a patient's temperature to a set target temperature. Water will be cooled or warmed as needed and pumped through one or more of the heat exchange devices so as to achieve the target temperature. As will be described in greater detailed below, depending on the programming provided to the system, multiple temperatures may be monitored (i.e. core body temperature, water temperature, blood temperature) and heating and cooling may be provided simultaneously in such manner as to provide optimize patient temperature control by multiple heat exchange devices. One heat exchange device may be employed to change the core body temperature, while another heat exchange device may provide cooling or heating to a particular area of the body such that the measured temperature does not fall below or exceed a particular target. In the patient temperature control mode, a master controller may be configured to provide this simultaneous control of a plurality heat exchange devices.

The water temperature control mode, automatically functions to flow temperature controlled water through the heat exchange devices. Water is controlled to a specific target temperature set by the operator. When activated, an indicator lights within button 116 will be illuminated. Unless an alarm condition occurs, heat exchange device and associated water temperature and flow rate will be displayed in the message screen 112 when this mode is active. In the master slave relationship described above, a user may employ the scroll buttons 108 and 110 to view the water temperature and other pertinent information for each of the interconnected temperature control systems.

The purge mode automatically functions to empty water from one or more of the heat exchange devices. When the mode is activated 80 light within button 118 will illuminate. A message (e.g. "purging water") will be displayed on the messages display screen 112 when this mode is active. When heat and other devices are empty, the system may then automatically returned to the stop mode.

Pressing the stop mode key 120 at any time will stop any of the three modes (i.e., patient temperature control, water temperature control mode, or purge modes). When activated, the yellow light within the stop mode key 120 will illuminate. Any other mode can be activated from stop mode by pressing the corresponding mode key.

A variety of system settings and other information may be accessed from menus and information listings displayed a message screen 104 in the Stop Mode, Water Temperature Control Mode, in Patient Treatment Mode, including e.g.:

1. Current patient temperature control mode;
2. Set patient target temperature;
3. Set water target temperature (for any of the heat exchange devices interconnected in the system);
4. Measured water level in any of the temperature control systems;
5. Set maximum/minimum water temperatures;
6. Set high and low patient temperature warning settings; and
7. Other set up parameters (e.g. data output intervals).

As may be appreciated, noted settings may be changed for each procedure. The settings may be further change during selected modes of operation. The system may be configured such that once the system has been turned off, settings are returned to default parameters. New default parameters can also be permanently saved if desired.

As noted above, the "up arrow" key 108 and the "down arrow" key one can allow users to scroll through menus and information listings on the message screen 530. Relatedly, the "Enter key" 112 allows an operator to select and change parameter settings. For example, a given parameter listed on the message screen 104 may be selected using arrow keys 108 and 110 and then the enter key 112 may be pressed, causing the parameter to be displayed in a pronounced manner (e.g. brightened or varied colored illumination). Further, the arrow keys 108 and 110 may be utilized to increase or decrease the setting value, respectively. When the desired value is displayed, the user may then a select the enter key 112 again to establish the setting. The "home key" 106 will exit a given menu and return a user back to a main menu when selected. The "alarm button" 124 is automatically illuminated upon detection of an order or alarm condition. Pressing this button will clear an alert or alarm.

According to the invention described herein, the two temperature control systems described herein are employable as stand alone units, which perform different functions. The blood/water heat exchange system is configured to monitor and provides temperature control for the blood of a patient on bypass. The control temperature control pad system is configured to provide heating and cooling of a patient's body through placement of pads on the exterior of a patient's body and then circulating a temperature controlled water through such pads at a predetermined temperature.

Certain situations exist where it would be desirable to optimize patient temperature control through providing heating and cooling to a number of different areas of a patient. The present system provides that capability through establishing a data connection between two or more patient temperature control systems. When two or more systems are connected in a master/slave relationship, or configured within a single device, temperature control may be provided in such a manner that the two systems work together to keep one or more monitored temperatures at a preprogrammed target valve. Using a data link established between the two or more systems, depending on the pre-provided programming, detected changes in temperature (whether they be in water temperature, or in patient temperature) are employable for adjusting either or both of the heat exchange devices so as to provide optimal temperature control.

Figure 6:
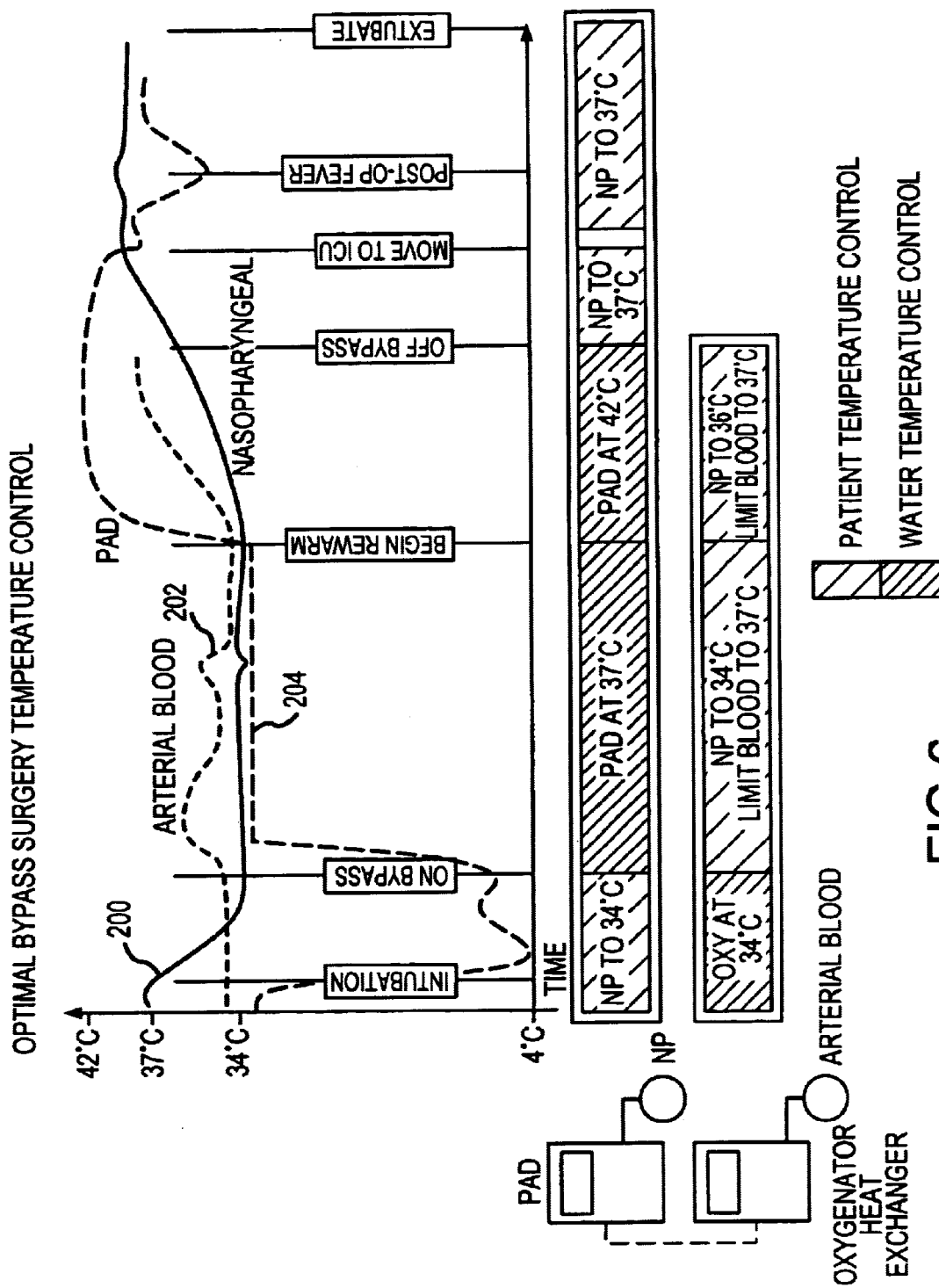
FIG. 6 discloses a graphical representation of arterial blood and pad temperatures in relation to poor body temperature during various portions of a cardiovascular surgery procedure.

An example of an optimal therapy which is employable by the system described herein, is described in the flow chart of FIG. 6 and the diagram of FIG. 7. The procedure described in this example is a cardiovascular surgical procedure which requires a patient to go on bypass. In the diagram of FIG. 7, the temperature shown are core body temperature 200, arterial blood temperature 202, and contact pad temperature 204, shown on a graph temperature vs. time. This diagram is marked to show the different stages of a cardiovascular surgical procedure.

Prior to the initiation of the surgical procedure, a system user may provide programming to the system which controls the operation of the overall system during certain portions of the procedure. The programming may include target core body temperatures and target water temperatures to be met and maintained during different parts of the procedure for the temperature control systems employed in the procedure. These values may be entered the through the display 100 of the temperature control system which will include the master controller. The system user through use of the up and down buttons 108 and 110 as well as the enter button 112 may scroll through various modes of operation for the temperature control systems and enter various values for target temperatures to be met during identified parts of the operation.

During a cardiovascular procedure, there are plurality of periods during which different target temperatures for the patient are to be met and sustained. Generally, these different periods may include intubation where the body is prepared to go on bypass, placing a patient on bypass and the time during bypass wherein the surgical procedure is performed, the rewarm of the body after the procedure is complete, removing the patient from a bypass, as well as the postoperative time period.

As an initial step in the process, the data link may be established between the systems and an indication of the link may be presented on one of the displays for the master temperature control system. Programming for various portions of the procedures may also be entered at this point. Once the temperature control systems are connected and programmed, they may be filled with water and the patient may then be prepared by positioning the temperature control pads in the appropriate position and a connection established to the core body temperature sensor.

As was mentioned above, the first step in this procedure is the intubation process (prior to cannulation). Initially, a patient can be cooled through the skin in advance of going on bypass. In this case, the pad controller may use the core temperature sensor for feedback. These initial stages of bypass can put the patient at risk due to manipulation of the aorta and cannulation of the arch. This can lead to breaking off calcified plaque from the wall, causing strokes or other blood vessels blockage. Dropping the patient's temperature immediately after intubation but before cannulation can bestow the benefit of hypothermia when needed. The priming solution in bypass circuit is maintained at 34C in anticipation of going on bypass.

Figure 5A:
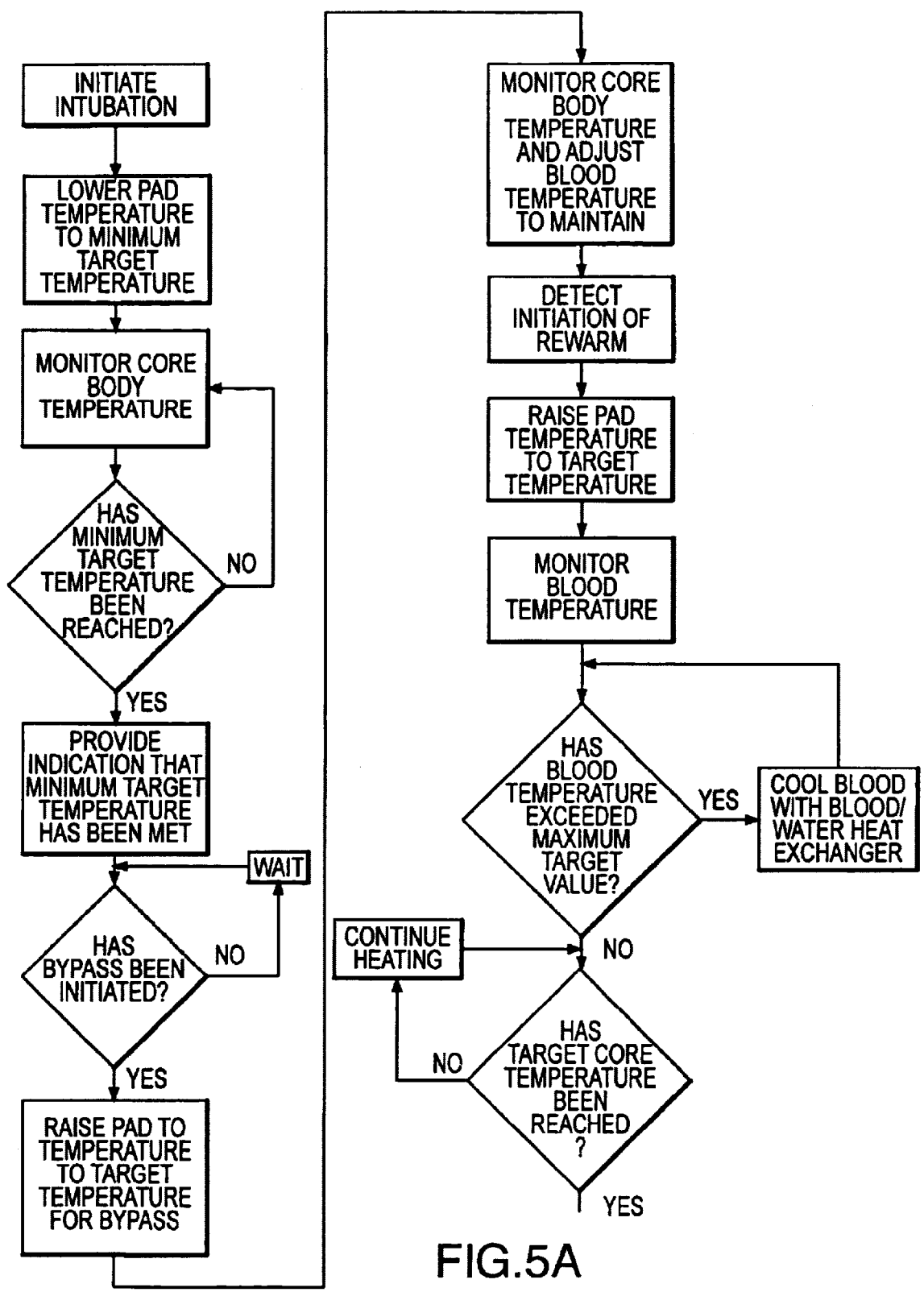
FIG. 5 discloses a flow chart which describes one pre-programmable procedure employable in a cardiovascular surgery.
Figure 5B:
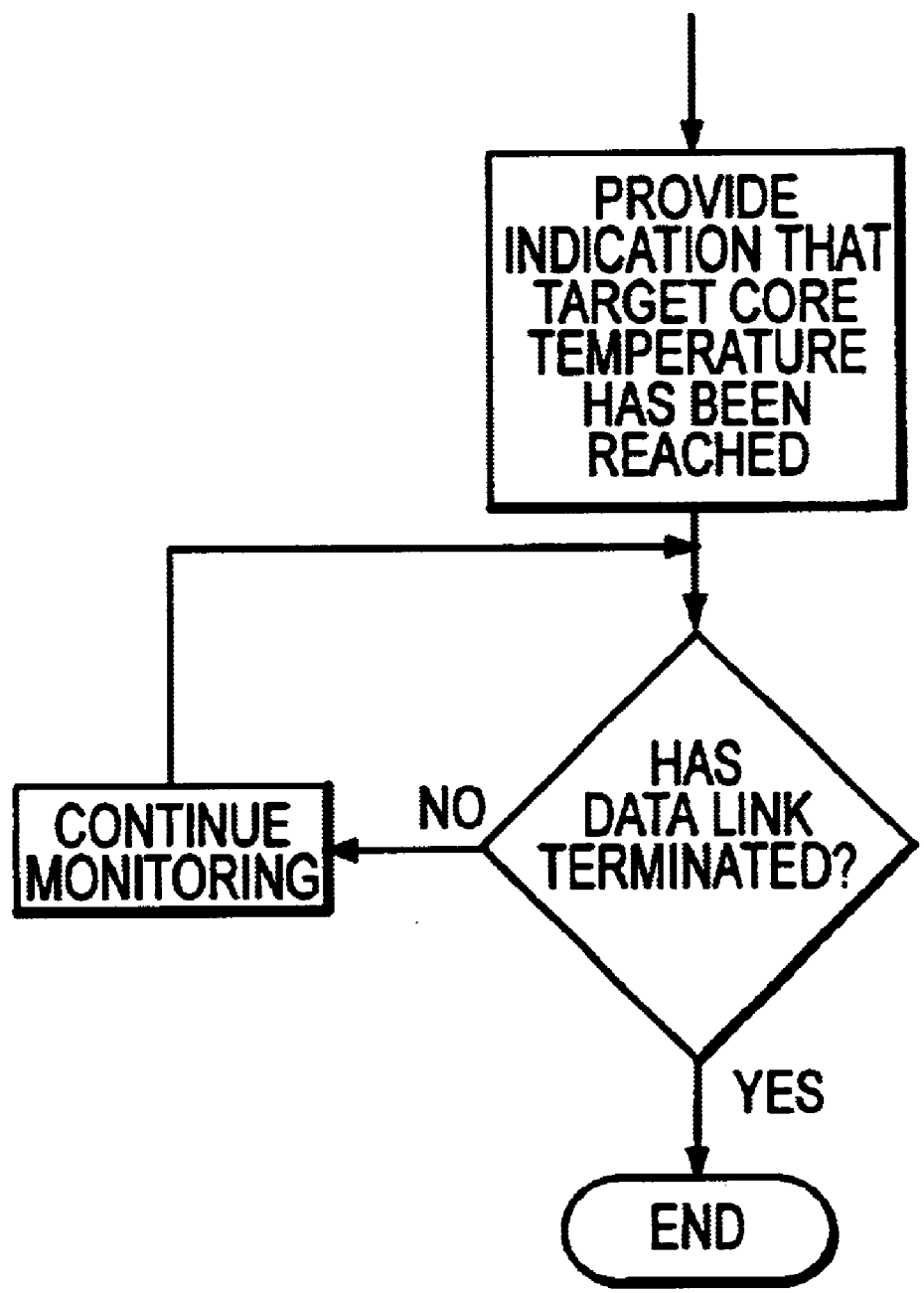

As an initial step as seen in flow chart of FIG. 5 the contact pad temperature is lower to a minimum amount. The core body temperature is then monitored until a target core body temperature has been reached. When the target core body temperature is reached, an indication may be presented on the display of the master temperature control system for the perfusionist. A second stage in the process may then be initiated, which is the patient going on heart-lung bypass. At this point, the perfusionist may scroll through the modes of operation presented on the display and select the next mode.

Once the bypass mode is initiated, the pad temperature can be raised to a programmed temperature in order to begin mild re-warm of the periphery. The patient core temperature may be maintained accurately by having the master controller receive the core temperature reading through the data link and adjusting water temperature according to a provided algorithm so as to maintain a desired blood temperature. In this case, the more heat which is transferred from the pads, the more cooling of the core is required through the blood/water heat exchanger. This monitoring process is continued throughout the surgical procedure so as to provide a constant core body temperature while providing warming up to be patient periphery.

Once the surgical procedure is complete the patient is prepared to come off bypass. The perfusionist may then initiate a re-warm process through a selection made on the display. During the re-warm, the contact pad temperature is raised to a higher temperature. The core temperature can be raised slowly and accurately into the normothermic range while limiting the maximum blood temperature. The control of the blood temperature may be provided through use of the blood/water heat exchanger. If it is detected that the blood temperature has exceed a preset value, a cooling process for the blood/water heat exchanger may be initiated. This cooling may be performed while still raising the pad temperature in a desired manner.

Once a target core temperature is reached, the patient may be taken off bypass and at that point the core temperature sensor is employed to monitor the core temperature. The pad controller uses this core temperature reading to raise the temperature to a target normothermic level. At this point, if the pad heat exchanger and the blood/water heat exchanger are contained in separate components, the data link may be terminated which is in turn indicated on the master controller display. The control pad temperature system may be used alone in order to raise the core body temperature to a desired value. The pad controller continues to use the core temperature sensor to manage temperature until extubation. Since a significant percentage of bypass patients experience a fever as a result of the bypass procedure, the pad controller may be used to control patient's temperature even after normothermia is initially achieved.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A system for providing optimized patient temperature control, comprising:

a plurality of patient temperature control systems, where each patient temperature control system in the plurality of patient temperature control systems is connectable to at least one heat exchange device and is configured to control heat exchange in a different region of a patient;

a central controller configured to receive signals for measured temperatures relating to patient condition from a plurality of patient temperature sensors, said controller further configured to generate and transmit control signals to the plurality of patient temperature control systems so as to simultaneously control the plurality of patient temperature control systems based on at least one of: the received signal for measured temperature relating to patient condition, programming provided for controlling operation of the plurality of patient temperature control systems, and manually inputted commands from a system operator; and said plurality of temperature control systems each further configured to receive the control signals and in response control the at least one heat exchange device connectable thereto.

2. The system of claim 1 wherein the plurality of measured temperatures comprise at least one of: a core body temperature, a blood temperature, and a temperature for a heat exchange medium employed in the heat exchange device.

3. The system of claim 1 wherein the controller is further configured to generate control signals for controlling the heat transfer according to a preprogrammed sequence.

4. The system of claim 3 wherein the central controller comprises a controller for one of the plurality of temperature control systems.

5. The system of claim 4 wherein each of the plurality of temperature control systems are connectable to the central controller via a data link.

6. The system of claim 5 wherein the data link comprises at least one of: a cable between RS232 port incorporated in each of the plurality of temperature control systems and a wireless communications link.

7. The system of claim 5 wherein the plurality of temperature control systems are configured to operate independently when the data link is terminated.

8. The system of claim 1 wherein the at least one heat exchange device comprise at least one of: a water/blood heat exchanger system and at least one temperature control pad transfer positionable on the patient's periphery.

9. The system of claim 8 wherein the controller is further configured to control the heat transfer by at least one of: employing a water temperature sensor in the water circulation system for both the water/blood heat exchanger system and the energy transfer pad system, and a predictive algorithm which predicts water temperature for the water in the water circulation system for both the water/blood heat exchanger system and the energy transfer pad system.

10. The system of claim 1 further including a user interface connectable to the central controller which provides for at least one of: monitoring of the measured temperatures and manual entry of commands for controlling the heat exchange devices.

11. The system of claim 1 wherein the plurality of temperature control systems are configurable in a single stand alone unit also including the central controller.

12. A method of controlling patient body temperature comprising the steps of:

configuring a plurality of temperature control systems each with at least one heat exchange devices to provide heat exchange to a designated region of the patient;

monitoring at least one selected temperature relating to patient condition and transmitting a temperature signal relating to the at least one temperature to a central controller in electrical communication with the plurality of temperature control systems;

identifying a first mode of operation from a plurality of modes of operation for providing patient temperature control wherein the at least one mode includes at least one target temperature; and simultaneously controlling the plurality of temperature control systems so as to provide the heat exchange according to the identified mode of operation until the at least one selected temperature is substantially equal to the target temperature.

13. The method of claim 12 wherein the selected temperatures comprise at least one of: a core body temperature, a blood temperature, and a temperature for a heat exchange medium employed in the heat exchange devices.

14. The method of claim 13 wherein the heat transfer is controlled through use of a predictive algorithm which predicts blood temperature based on water temperature in the blood/water heat exchanger.

15. The method of claim 12 wherein the plurality of heat exchange devices comprise at least one of: a water/blood heat exchanger and at least one temperature control pad positionable on the patient's periphery.

16. The method of claim 12 wherein the central controller is configured in one of the plurality of temperature control systems.

17. The method of claim 16 further comprising the steps of:

establishing a data link between the temperature control system with the central controller and one other of the temperature control systems; and establishing a master/slave relationship between the temperature control system with the central controller and the one other temperature control system.

18. The method of claim 17 wherein the plurality of modes of operation include at least one of:

employing the temperature control pad to lower the patient core body temperature;

employing the temperature control pad to warm the patient periphery while maintaining the desired temperature for the core temperature through use of the water/blood heat exchanger;

employing both the temperature control pad and the blood/water heat exchanger simultaneously to affect the body core temperature.

19. The method of claim 12 wherein the target temperature is identified through receipt of a value manually inputted through a user interface.

20. The method of claim 12 further comprising the step of manually initiating the mode of operation through manual input received through a user interface.

21. The method of claim 12 further comprising the step of presenting on the user interface at least one of: the at least one selected temperature and the mode of operation.

22. A system for controlling patient temperature comprising:
- a first temperature control system including a first controller, wherein the first temperature control system is connectable to at least one first heat exchange device for providing heat exchange in a first designated region of the patient and at least one first patient temperature sensor which provides temperature signals relating to patient condition;
- a second temperature control system including a second controller, wherein the second temperature control system is connectable to at least one second heat exchange device for providing heat exchange in a second designated region of the patient and at least one second patient temperature sensor which provides temperature signals relating to the patient condition; and
- at least one data link establishable between the first and second controller wherein the data link provides for the transfer of control signals between the first and second controller so as to provide for the heat exchange in at least one of the first and second regions in response to signals for measured temperatures received by the first and second controllers from at least one of the first and second sensors.

23. The system of claim 22 wherein the first heat exchange device comprises a water/blood heat exchanger system and the second heat exchange device comprises at least one temperature control pad positionable on the patient's periphery.

24. The system of claim 22 wherein at least one of: the first controller is further configured as a central controller for the first and second temperature control systems when the data link is established, and wherein the central controller is configured to receive and process signals from the at least one second sensor and to transmit control signals over the data link to control the heat transfer of the second heat transfer device.

25. The system of claim 22 wherein the first and second temperature sensors are configured to measure at least one of: core body temperature, a blood temperature, and a temperature for a heat exchange medium employed in either the first or second heat exchange device.

26. The system of claim 22 further including a user interface connectable to at least one of: the first and second controller, which provides for at least one of: monitoring of the measured temperatures and manual entry of commands for controlling the first and second heat exchange devices.

27. The system of claim 22 wherein the data-link is further configured to be disconnectable so that the first and second temperature control systems may operate independently.

28. The system of claim 22 wherein the first and second temperature control systems are combinable in a stand alone device.

29. The system of claim 22 wherein the at least one first heat exchange device and the at least one second heat exchange device are configured for simultaneous heat exchange in the first and second designated regions so as to provide for optimized patient temperature control.

* * * * *